United States Patent [19]

Sagemuehl et al.

[11] Patent Number: 4,630,321
[45] Date of Patent: Dec. 23, 1986

[54] SAFETY SPECTACLES WITH BROW PROTECTOR

[75] Inventors: Hans W. Sagemuehl, Cotuit; Kenneth G. Duffie, Middleboro, both of Mass.

[73] Assignee: H. L. Bouton Company, Inc., Buzzards Bay, Mass.

[21] Appl. No.: 854,244

[22] Filed: Apr. 21, 1986

[51] Int. Cl.[4] ................................................ A61F 9/02
[52] U.S. Cl. .......................................... 2/426; 2/431; 2/439; 2/449; 351/158
[58] Field of Search .................... 2/449, 431, 442, 426, 2/427, 443; 351/158

[56] References Cited

U.S. PATENT DOCUMENTS

| 2,590,397 | 3/1952 | Gay et al. | 2/443 |
| 3,133,982 | 5/1964 | Janz | 2/426 X |
| 4,547,909 | 10/1985 | Bell | 2/449 X |
| 4,556,995 | 12/1985 | Yamamoto | 2/439 |

FOREIGN PATENT DOCUMENTS

| 0457706 | 6/1949 | Canada | 2/439 |
| 0481478 | 3/1952 | Canada | 2/439 |
| 0753789 | 3/1967 | Canada | 2/449 |

Primary Examiner—Louis K. Rimrodt
Attorney, Agent, or Firm—Biebel, French and Nauman

[57] ABSTRACT

A pair of safety spectacles incorporates a brow-protecting bar member which is formed separately from the spectacle frame and is anchored thereto only at its ends, by means of the hinge pins attaching the temples to the frame. The frame and brow bar therefore have such freedom to flex back and forth with respect to each other as to provide a cushioning effect absorbing impact on the frame from the front after the brow bar engages the brow of the wearer, and this engagement is also made more comfortable by providing the brow bar with a brow-engaging flange of substantial height which extends the full length of the brow bar.

6 Claims, 6 Drawing Figures

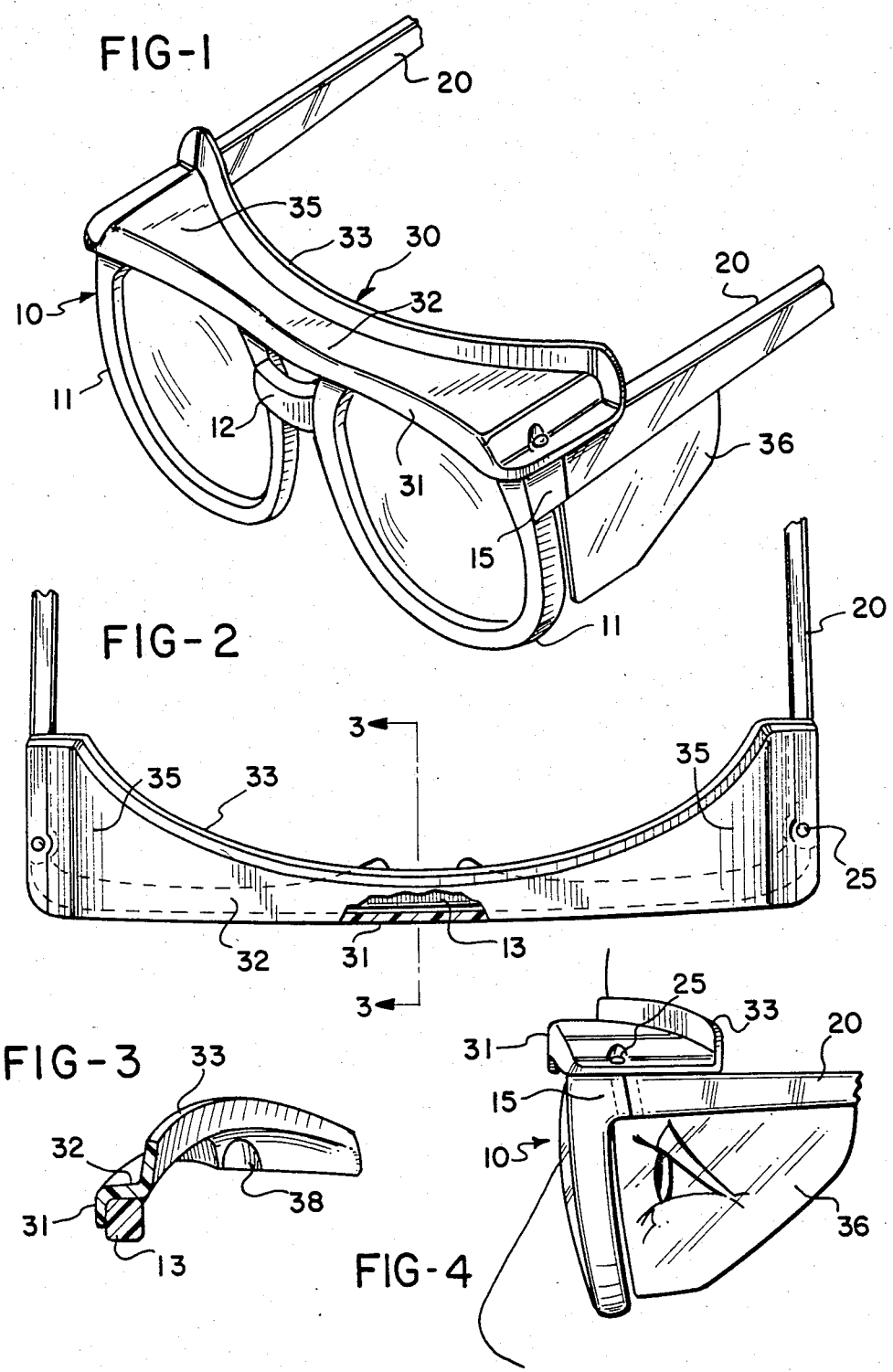

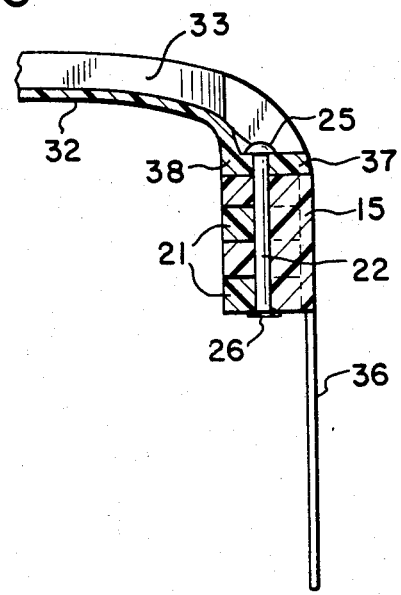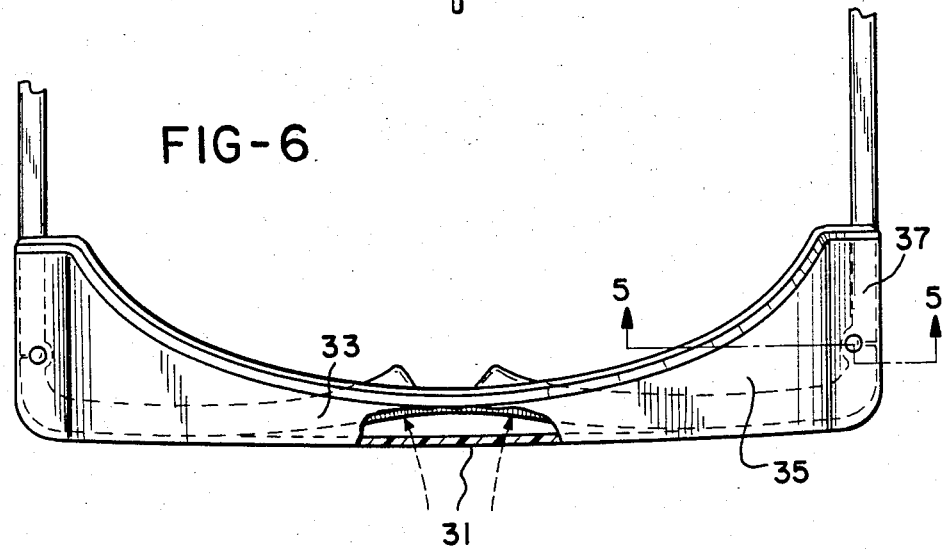

SAFETY SPECTACLES WITH BROW PROTECTOR

BACKGROUND OF THE INVENTION

This invention relates to safety spectacles for protecting both the eyes and also the adjacent areas of the human face against the impact or entry of foreign objects of the various types likely to be encountered in industrial work.

It has been relatively common in the past to provide protective spectacles for both industrial and sports wear with some sort of bar at the top of the frame which is designed to bear against the brow of the wearer, or to move against the brow in response to impact from the front in order to distribute the effect of such impact over a correspondingly large area of the face. To the best of the present inventor's knowledge, all such prior arrangements have involved either a relatively rigid bar fixedly mounted on the frame or actually forming a part of the frame, or a piece of relatively spongy material.

SUMMARY OF THE INVENTION

The present invention provides an improved safety spectacle construction wherein a brow-protecting bar is initially formed separately from the frame, but is assembled thereto by anchoring its opposite ends to the ends of the frame, as by means of the hinge pins which connect the temples to the ends of the frame. This brow protector includes a vertically extending flange of substantial vertical dimensions which is curved and proportioned to fit smoothly against the brow of the wearer across the front and also at both ends of the frame. However, the brow protector is secured to the spectacle frame only at its ends so that their respective portion can flex with respect to each other in response to impact on the frame from the front.

These two features provide outstanding advantages in the use of the safety spectacles of the invention. Under normal wearing conditions, the bridge will support the frame on the nose of the wearer, with the brow protector close to but spaced from the wearer's brow. In the event of impact from the front, the frame as a whole will tend to move back and up until the brow protector seats on the wearer's brow, thereby distributing the impact over a relatively wide area.

If the impact is continued or severe, the frame and bridge can still move backward somewhat further, but this movement will be cushioned by flexing of the frame, since its ends cannot move back any further. This flexing of the frame, as its central portion moves inwardly with respect to the brow protector, will absorb and cushion the severity of the impact.

Other objects and advantages of the invention will be pointed out in connection with the description of the preferred embodiment of the invention.

BRIEF DESCRIPTION OF THE DRAWING

FIG. 1 is a perspective view of safety spectacles embodying the present invention;

FIG. 2 is a plan view of the spectacle shown in FIG. 1;

FIG. 3 is a section on the line 3—3 of FIG. 2;

FIG. 4 is a fragmentary side view of the spectacles shown in FIG. 1;

FIG. 5 is an enlarged section on the line 5—5 of FIG. 6; and

FIG. 6 is a somewhat diagrammatic view from the top illustrating the operation of the brow-protecting portion of the spectacle in cushioning impact on the front of the frame.

DESCRIPTION OF THE PREFERRED EMBODIMENT

The spectacle frame 10 is molded from suitable plastic, such as the cellulose acetate butyrate sold as "Tenite 556" by Eastman Chemical Co. The frame includes the usual pair of lens-receiving rims 11 connected by a bridge which may be of any conventional design and is shown as a lower portion 12 shaped to seat on the wearer's nose, and an upper bar portion 13 which forms a continuation of the tops of the lens rims. Each end of the frame includes an integral boss 15 which forms one part of the hinge means connecting the frame to a temple 20 of any desired design. Each temple includes a complementary hinge part 21, and a hinge pin 22 completes each hinged connection. The hinge pin 22 is shown as having an enlarged head 25, and it may be threaded into the hinge parts or have its lower end expanded in rivet fashion as shown at 26 in FIG. 5.

The brow-protecting part 30 of the spectacle, which for convenience is referred to as the "brow bar" hereafter, is initially molded separately from the frame of suitable hard plastic material of moderate flexibility. The brow bar 30 is generally Z-shaped in vertical section throughout the major part of its length, and it includes a vertical front flange 31 overlying the front of the hinge bar 13 and the tops of the lens rims 11, a horizontal middle portion 32 which overlies the top of the frame 10, and a vertical rear flange 33 extending upwardly from the middle portion 32.

As best shown in FIG. 2, the middle portion 32 of the brow bar is of minimum width above the bridge and of increasing width towards each end thereof to provide the vertical flange 33 with a curved shape as viewed from above to fit the brow of the wearer and also to extend around each side of the brow. This in turn provides the middle portion 32 of the brow bar with web portions 35 at each end which cover the space between the brow of the wearer and each of the temples 20 in the expanded, operating position of the temples, and which thus cooperate with the side shields 36 depending from the temples.

The web portions 35 of the brow bar terminate in horizontal flanges 37 which seat on the tops of the hinge bosses 15 and are anchored thereto by the hinge pins 22, each flange 37 having a partially cylindrical boss 38 on its underside which stabilizes the junction between flange 36 and boss 15 and also forms a bearing for pin 22. The remainder of the brow bar, however, has no direct connection to the frame 10 except that the middle flange 32 seats on top of the frame, and the front flange 31 is normally in contact with the front of the upper part of the frame, at least at the two ends of the frame.

With this construction, when the spectacle as a whole is in the normal position on the wearer's face, the flange 33 will be close to the brow of the wearer but generally spaced a slight distance in front of the brow. In the event of impact on any part of the frame, including the front of the brow bar, the spectacle will move back until the flange 33 engages the brow, but with this flange 33 of the extended length and substantial height shown in the drawing, the force of the impact will be distributed over a correspondingly wide area to minimize the causing of discomfort.

If the impact should be relatively severe or sustained, the same action will initially occur, but as soon as the brow bar flange 33 has seated against the face of the wearer, continued force on the frame can cause the center part of the frame to move inwardly with respect to the front flange 31, as illustrated in FIG. 6. During such action, the frame as a whole will flex resiliently, and the outer end portions of the brow bar can similarly flex outwardly to a limited extent, so that the frame and brow bar combine to absorb the force of the impact as they flex to provide a cushioning effect.

It will be apparent that the material from which both the frame and the brow bar are formed should be selected to provide the desired characteristics of relative rigidity but with limited resilient flexibility, and satisfactory results from this standpoint have been obtained with the brow bar also molded from the same "Tenite 556" material as the frame. The proportions of the brow bar as a whole should of course be properly matched with those of the spectacle frame to which it is to be attached, and it can therefore be made in a variety of sizes. It is important, however, that the height of the vertically extending flange 33 be sufficient to provide the desired extensive contact area against the brow of the wearer, and from this standpoint, the flange 33 should be at least approximately a quarter inch in height over substantially its entire length, including its curved end portins which are located to engage the side portions of the brow.

While the product herein described constitutes a preferred embodiment of the invention, it is to be understood that the invention is not limited to this precise product, and that changes may be made therein without departing from the scope of the invention which is defined in the appended claims.

What is claimed is:

1. A protective spectacle comprising:
   (a) a frame including a pair of lens-receiving rims connected by a bridge,
   (b) a temple connected to each end of said frame by hinge means,
   (c) a brow-protecting bar separate from and extending along the full length of the top of said frame with the ends thereof seated on end portions of said frame, and
   (d) means anchoring said bar ends to said frame while leaving the remainder of said bar free of said frame,
   (e) whereby in response to impact on the front of said frame, said frame can move toward the face of the wearer after said bar engages the brow of the wearer.

2. A protective spectacle as defined in claim 1 wherein said hinge means for each said temple includes a boss integral with said frame, and wherein said bar ends seat on and are anchored to the tops of said bosses.

3. A protective spectacle as defined in claim 2 wherein each of said hinge means includes a hinge pin, and said pins extend through said ends of said bar to anchor said bar ends to said bosses.

4. A protective spectacle as defined in claim 1 wherein said bar is generally Z-shaped in vertical section to provide a front flange overhanging the front of said rims and bridge, a middle portion overlying the top of said frame, and a rear flange extending upwardly from said middle portion of said bar in position for engagement with the brow of the wearer.

5. A protective spectacle as defined in claim 4 wherein said upwardly extending rear flange extends along the full length of said bar to provide a correspondingly substantial area for contact with the brow of the wearer, and wherein said middle portion of said bar is of minimum width above said bridge and of increasing width toward each end thereof to provide said rear flange with a curved shape as viewed from above to fit the brow of the wearer and also to provide a web portion covering the space between the brow of the wearer and each of said hinge means.

6. A protective spectacle comprising:
   (a) a frame including a pair of lens-receiving rims connected by a bridge,
   (b) a temple connected to each end of said frame by hinge means including a boss integral with said frame,
   (c) a brow-protecting bar separate from and extending along the full length of the top of said frames with the ends thereof seated on the tops of said bosses,
   (d) said bar being generally Z-shaped in vertical section to provide a front flange overhanging the front of said rims and bridge, a middle portion overlying the top of said frame, and a rear flange extending upwardly from said middle portion of said bar in position for engagement with the brow of the wearer,
   (e) said rear flange extending along the full length of said bar to provide a correspondingly substantial area for contact with the brow of the wearer,
   (f) said middle portion of said bar being of minimum width above said bridge and of increasing width toward each end thereof to provide said rear flange with a curved shape as viewed from above to fit the brow of the wearer and also to provide a web portion covering the space between the brow of the wearer and each of said hinge means, and
   (g) each of said hinge means including a hinge pin extending through the adjacent end of said bar to anchor said bar ends to said bosses,
   (h) whereby in response to impact on the front of said frame, said bar is free to flex as said frame moves toward the face of the wearer after said bar engages the brow of the wearer and thereby absorbs and cushions such impact.

* * * * *